(12) United States Patent
Karo et al.

(10) Patent No.: US 8,600,474 B2
(45) Date of Patent: Dec. 3, 2013

(54) BODY FAT MEASUREMENT DEVICE

(75) Inventors: Hiromichi Karo, Kyoto (JP); Takehiro Hamaguchi, Kyoto (JP); Kazuhisa Tanabe, Kyoto (JP); Yasuaki Murakawa, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/817,241

(22) PCT Filed: Jun. 22, 2011

(86) PCT No.: PCT/JP2011/064283
§ 371 (c)(1),
(2), (4) Date: Feb. 15, 2013

(87) PCT Pub. No.: WO2012/023340
PCT Pub. Date: Feb. 23, 2012

(65) Prior Publication Data
US 2013/0190588 A1 Jul. 25, 2013

(30) Foreign Application Priority Data
Aug. 17, 2010 (JP) ................................ 2010-182358

(51) Int. Cl.
*A61B 5/053* (2006.01)
(52) U.S. Cl.
USPC ............................ 600/382; 600/393; 600/547
(58) Field of Classification Search
USPC .......................................... 600/382, 393, 547
See application file for complete search history.

(56) References Cited

U.S. PATENT DOCUMENTS

| 6,840,907 | B1 * | 1/2005 | Brydon ........................ 600/534 |
| 6,850,798 | B2 * | 2/2005 | Morgan et al. ................ 600/547 |
| 2003/0176808 | A1 * | 9/2003 | Masuo .......................... 600/547 |
| 2005/0222516 | A1 | 10/2005 | Kasahara et al. |
| 2006/0015027 | A1 * | 1/2006 | Matthews et al. ............. 600/393 |
| 2008/0021349 | A1 * | 1/2008 | Sakai et al. ................... 600/587 |

(Continued)

FOREIGN PATENT DOCUMENTS

| JP | 2002-369806 A | 12/2002 |
| JP | 2003-319916 A | 11/2003 |

(Continued)

OTHER PUBLICATIONS

Official Communication issued in International Patent Application No. PCT/JP2011/064283, mailed on Sep. 13, 2011.

*Primary Examiner* — Lee S Cohen
*Assistant Examiner* — Erin M Cardinal
(74) *Attorney, Agent, or Firm* — Keating & Bennett, LLP

(57) ABSTRACT

A body fat measurement device includes a back area electrode group support unit including back area electrodes arranged to contact a back area of a measurement subject, a trunk area dimension measurement unit that detects the width and depth of a trunk area of the measurement subject, a position detection unit that detects a relative positional relationship between the back area electrode group support unit and the trunk area dimension measurement unit, an electrode selection unit that selects specific electrodes, placed in contact with the back area at an area that corresponds to the location of the navel of the measurement subject, from a plurality of electrodes included in a trunk area electrode group, based on the position information detected by the position detection unit, and a body impedance measurement unit that measures a body impedance of the measurement subject using the selected back area electrodes.

8 Claims, 8 Drawing Sheets

(56) References Cited

U.S. PATENT DOCUMENTS

| | | |
|---|---|---|
| 2008/0194982 A1* | 8/2008 | Lanfermann et al. ......... 600/547 |
| 2008/0221474 A1* | 9/2008 | Waffenschmidt et al. .... 600/547 |
| 2008/0221476 A1* | 9/2008 | Sakai ............................ 600/547 |
| 2009/0024014 A1 | 1/2009 | Sugo et al. |
| 2009/0024053 A1 | 1/2009 | Kasahara |
| 2009/0216140 A1* | 8/2009 | Skrabal ......................... 600/509 |
| 2010/0081962 A1 | 4/2010 | Hamaguchi et al. |
| 2010/0121216 A1 | 5/2010 | Hamaguchi et al. |
| 2010/0168530 A1* | 7/2010 | Chetham et al. ............. 600/301 |

FOREIGN PATENT DOCUMENTS

| | | |
|---|---|---|
| JP | 2005-288023 A | 10/2005 |
| JP | 2008-023232 A | 2/2008 |
| JP | 2008-228890 A | 10/2008 |
| JP | 2008-228996 A | 10/2008 |
| JP | 2008-295881 A | 12/2008 |
| JP | 2009-000534 A | 1/2009 |
| JP | 2009-022482 A | 2/2009 |
| JP | 2009-225854 A | 10/2009 |
| WO | 2008/123042 A1 | 10/2008 |

* cited by examiner

BODY FAT MEASUREMENT DEVICE

BACKGROUND OF THE INVENTION

1. Field of the Invention

The present invention relates to body fat measurement devices configured to be capable of calculating a body fat mass of a measurement subject by measuring a body impedance, and particularly relates to body fat measurement devices configured to be capable of measuring a body fat mass such as a visceral fat mass with ease.

2. Description of the Related Art

In recent years, body fat mass is gaining attention as an indicator used to determine the health of a measurement subject. In particular, visceral fat mass is gaining attention as an indicator for determining whether or not a person is suffering from central obesity. Central obesity is said to bring about lifestyle-related diseases that can easily lead to artery hardening, such as diabetes, hypertension, and hyperlipidemia, and the stated indicators hold promise in terms of preventing such diseases. "Visceral fat" refers to fat that accumulates around the internal organs on the inner side of the abdominal muscles and the back muscles, and is distinct from the subcutaneous fat that is located toward the surface of the trunk area. It is typical to employ the area occupied by visceral fat in a cross-section of the trunk area that corresponds to the navel (referred to as a "visceral fat cross-sectional area" hereinafter) as an indicator of the visceral fat mass.

Normally, visceral fat mass is measured by analyzing images obtained through X-ray computed tomography (CT), magnetic resonance imaging (MRI), or the like. In such image analysis, the visceral fat cross-sectional area is calculated geometrically from a tomographic image of the trunk area obtained by using X-ray CT, MRI, or the like. However, it is necessary to use several pieces of large equipment installed in a medical facility, such as X-ray CT, MRI, or other machines, in order to make use of such a measurement method; thus it is extremely difficult to measure visceral fat mass on a daily basis through such a measurement method. X-ray CT also poses the problem of exposure to radiation, and thus cannot necessarily be called a desirable measurement method.

A body impedance technique is being considered as an alternative to these measurement methods. The body impedance technique is a method for measuring body fat mass widely used in household-based body fat measurement devices; in this technique, electrodes are placed in contact with the four limbs, the body impedance is measured using those electrodes, and the body fat mass is calculated from the measured body impedance. The stated household body fat measurement device makes it possible to accurately measure the extent of body fat buildup throughout the entire body or in specific areas such as the four limbs, the trunk area, or the like.

However, conventional body fat measurement devices that use the body impedance technique measure the extent of body fat buildup throughout the entire body or in specific areas such as the four limbs, the trunk area, or the like, as mentioned earlier, and are not capable of accurately extracting and measuring the extent of visceral fat buildup, the extent of subcutaneous fat buildup, and the like individually. This is because, as mentioned above, conventional body fat measurement devices are configured so that the electrodes are attached only to the four limbs, and thus the visceral fat and subcutaneous fat cannot be accurately measured individually.

Accordingly, bringing electrodes into direct contact with the trunk area, measuring the body impedance using those electrodes, and individually and accurately calculating the visceral fat mass and the subcutaneous fat mass based on that measurement is being considered as a way to solve this problem.

For example, JP 2002-369806A discloses a body fat measurement device configured so that electrodes are provided on the inner circumferential surface of a belt member and the belt member is wrapped around and anchored to the trunk area of a measurement subject, thus placing the electrodes in contact with the trunk area.

Meanwhile, JP 2005-288023A, JP 2008-23232A, and so on disclose body fat measurement devices configured so that electrodes are provided on the surface of a fitting unit that is fitted to the abdominal area of a measurement subject and the fitting unit is pressed against the abdominal area, thus placing the electrodes in contact with the abdominal area.

Furthermore, JP 2008-295881A discloses a body fat measurement device configured so that electrodes are provided on the inner circumferential surface of a belt member and the belt member is wrapped around and affixed to a measurement subject's trunk area, and electrodes are provided on clip-shaped members and the clip-shaped members are affixed to the measurement subject's arms and legs, thus placing electrodes in contact with the abdominal area and arms and legs of the measurement subject, who is lying face-up.

In addition, although not discussing a specific device configuration, JP 2008-228890A mentions being able to accurately measure visceral fat mass and subcutaneous fat mass by placing electrodes in contact with the back of a measurement subject's trunk area (that is, the back) without placing electrodes in contact with the measurement subject's abdominal area and placing electrodes in contact with the arms and legs of the measurement subject, measuring the body impedance, and calculating the visceral fat mass and the subcutaneous fat mass based on the measured body impedance. One of the reasons for this is that the subcutaneous fat that accumulates on the abdominal area side is relatively thinner than the subcutaneous fat that accumulates on the back area side, and thus if the electrodes are placed in contact with the abdominal area, the current that is applied will flow through fat-free areas, which makes it easy for errors to occur.

Meanwhile, to make it possible to measure the visceral fat mass, subcutaneous fat mass, and so on with a high degree of accuracy using the stated body impedance, it is necessary to take actual measurements of the measurement subject's trunk area body build, such as the circumferential length of the trunk area, the trunk area width, and the trunk area depth, and use the measurements in computation processes for calculating the body fat mass.

For example, according to the body fat measurement device disclosed in the stated JP 2005-288023A, a fitting unit that is fitted to a measurement subject's abdominal area is provided upon a pair of arm portions, which make contact with both sides of the measurement subject's trunk area (in other words, both flanks), so that the fitting unit is mobile; the trunk area width is measured by bringing the arm portions into contact with both flanks, and the result of that actual measurement is used in computation processes for calculating body fat mass.

In addition, according to the body fat measurement device disclosed in the stated JP 2008-23232A, a fitting unit that is fitted to a measurement subject's abdominal area is provided upon an arm portion, which makes contact with the measurement subject's back, so that the fitting unit is mobile; the trunk area depth is measured by bringing the arm portion into contact with the back, and the result of that actual measurement is used in computation processes for calculating body fat mass.

Furthermore, in the body fat measurement device disclosed in the aforementioned JP 2008-295881A, an actual measurement of the circumferential length of the trunk area is taken by detecting the length at which the belt member worn on the trunk area of the measurement subject is wrapped, and the result of that actual measurement is used in computation processes for calculating a body fat mass.

As described above, it is necessary to bring electrodes into contact with a measurement subject's trunk area and take an actual measurement of the measurement subject's body build at the trunk area, as represented by the circumferential length of the trunk area, the trunk area width, the trunk area depth, and so on, in order to measure a visceral fat mass and the like with a high level of accuracy through the body impedance technique. To measure the visceral fat mass and the like more accurately at this time, it is essential to position the electrodes that are to be placed in contact with the measurement subject's trunk area precisely on the trunk area, and to position a distance measurement means for actually measuring the measurement subject's body build precisely around the trunk area.

In the case where, for example, the electrodes have not been correctly positioned relative to the measurement subject's trunk area, the measured body impedance will contain a high degree of error, resulting in a high degree of error in the calculated visceral fat mass or the like. Furthermore, in the case where, for example, the distance measurement means has not been correctly positioned relative to the measurement subject's trunk area, the measured body build information of the measurement subject's trunk area will contain a high degree of error, resulting in a high degree of error in the calculated visceral fat mass or the like. Accordingly, the body fat measurement device is normally configured so that the electrodes, distance measurement means, and so on are positioned using the measurement subject's navel as a reference, and the body fat measurement device employs a configuration in which various types of indicators and the like used for this positioning are provided.

Here, in the case where the electrodes to be placed in contact with the trunk area and the distance measurement means are to be integrated into a single unit, as disclosed in the aforementioned JP 2005-288023A, JP 2008-23232A, and JP 2008-295881A, both the electrodes and the distance measurement means are to be precisely positioned relative to the trunk area through a single positioning operation.

However, with the body fat measurement devices disclosed in the aforementioned JP 2005-288023A and JP 2008-23232A, in the case where actual measurements of the trunk area width and the trunk area depth are to be taken by bringing the arm portions provided in a mobile state into contact with the trunk area, the measurement subject or the like is forced to carry out operations for individually moving the arm portions along two directions of the trunk area, or the forward/backward direction and the right/left direction; thus there is a problem in that the body fat measurement device is not necessarily easy to use. These operations become extremely complicated particularly in the case where the body fat measurement device is configured so that the measurement subject him/herself can perform the measurement alone, without the help of an assistant or the like; this greatly inhibits taking measurements of a visceral fat mass or the like in a simple and easy manner.

Meanwhile, in the case where the configuration is such that an actual measurement is taken of the circumferential length of the trunk area using a belt member in which electrodes are provided, as with the body fat measurement device disclosed in the aforementioned JP 2008-295881A, the measurement subject or the like is forced to perfectly wrap the belt member around his/her trunk area at the proper wrapping strength; thus there is a problem in that the body fat measurement device is not necessarily easy to use. Note that it is preferable to employ the trunk area width and trunk area depth, using which the cross-sectional area of the measurement subject's trunk area can be estimated more accurately, as the body build information that should be measured for the measurement subject; from this point of view, the body fat measurement device disclosed in the aforementioned JP 2008-295881A has room for improvement.

In this manner, conventional body fat measurement devices have not necessarily been easy to use, and have been problematic in that accurate body fat measurement could not be carried out in an easily-repeatable manner.

SUMMARY OF THE INVENTION

Having been achieved in order to solve the stated problems, it is an object of the present invention to provide a body fat measurement device that is capable of accurately measuring body fat masses such as visceral fat mass and that is easy to operate and use when taking such measurements.

A body fat measurement device according to the present invention includes a trunk area electrode group, a trunk area electrode group support unit, a trunk area dimension detection unit, a trunk area dimension measurement unit, a position detection unit, an electrode selection unit, a body impedance measurement unit, and a body fat mass calculation unit. The trunk area electrode group includes a plurality of electrodes for making contact with the surface of a measurement subject's trunk area. The trunk area electrode group support unit is a unit for bringing at least some of the plurality of electrodes included in the trunk area electrode group into contact with the measurement subject's trunk area, and the trunk area electrode group is provided in the trunk area electrode group support unit. The trunk area dimension detection unit is a unit for detecting a trunk area dimension of the measurement subject. The trunk area dimension detection unit is provided in the trunk area dimension measurement unit. The position detection unit is a unit that detects a relative positional relationship between the trunk area electrode group support unit and the trunk area dimension measurement unit, whereas the electrode selection unit is a unit that selects specific electrodes from the plurality of electrodes included in the trunk area electrode group based on the position information detected by the position detection unit. The body impedance measurement unit is a unit that measures a body impedance of the measurement subject's body using the electrodes selected by the electrode selection unit, whereas the body fat mass calculation unit is a unit that calculates a body fat mass based on the body impedance measured by the body impedance measurement unit and the trunk area dimension detected by the trunk area dimension detection unit.

Preferably, the body fat measurement device according to the present invention further includes a guidance mechanism that guides the trunk area dimension measurement unit so as to be movable along the body axis direction of the measurement subject's trunk area.

In the body fat measurement device according to the present invention, it is preferable for the trunk area electrode group support unit to be configured of a mat that can be disposed below the measurement subject's trunk area when the measurement subject is lying down, and in such a case, it is preferable for the trunk area dimension measurement unit to be configured of a frame-shaped member that can be disposed so as to surround the measurement subject's trunk area when the measurement subject is lying down.

In the body fat measurement device according to the present invention, in the case where the trunk area electrode group support unit is configured of the stated mat, it is preferable for the plurality of electrodes included in the trunk area electrode group to be disposed in rows on a primary surface of the mat.

In the body fat measurement device according to the present invention, in the case where the trunk area dimension measurement unit is configured of the stated frame-shaped member, it is preferable for the trunk area dimension detection unit to be configured of a non-contact range sensor disposed on the frame-shaped member.

In the body fat measurement device according to the present invention, in the case where the trunk area dimension measurement unit is configured of the frame-shaped member, it is preferable for the trunk area dimension measurement unit to be disposed so as to be positioned at the location of the measurement subject's navel during measurement.

In the body fat measurement device according to the present invention, it is preferable for the configuration to be such that the electrode selection unit selects, as the specific electrodes, electrodes, from among the plurality of electrodes included in the trunk area electrode group, that are disposed in an area corresponding to the location of the measurement subject's trunk area at which the trunk area dimension is detected using the trunk area dimension measurement unit.

In the body fat measurement device according to the present invention, it is preferable for the plurality of electrodes included in the trunk area electrode group to be electrodes for making contact with a surface of a back area that is an area of the measurement subject's trunk area on a back side.

In the body fat measurement device according to the present invention, it is preferable for the body fat mass calculation unit to include at least one of a visceral fat mass calculation unit that calculates the visceral fat mass of the measurement subject and a subcutaneous fat mass calculation unit that calculates the subcutaneous fat mass of the measurement subject.

According to the present invention, it is possible to realize a body fat measurement device that is capable of accurately measuring body fat masses such as visceral fat mass and that is easy to operate and use when taking such measurements.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1A:
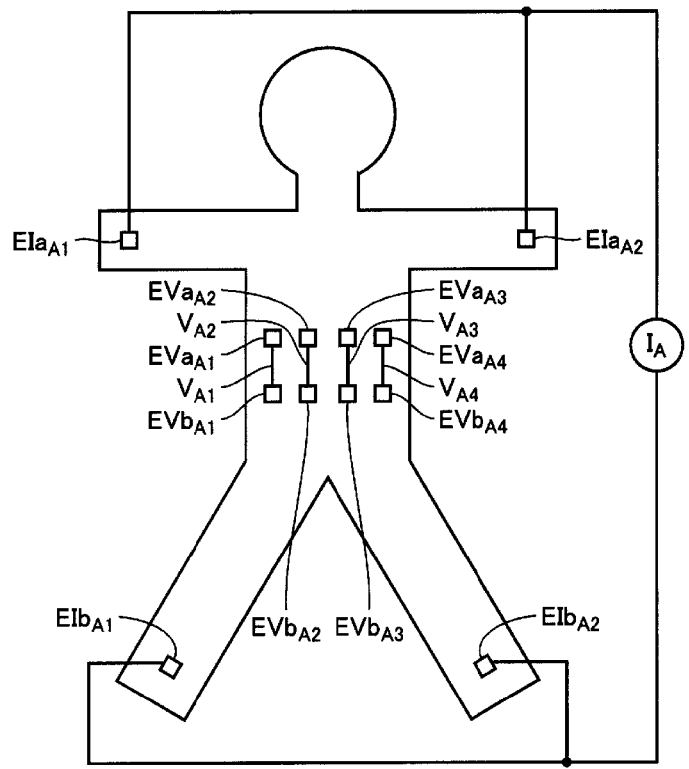
FIG. 1A is schematic a diagram illustrating the fundamentals of measurement performed by a body fat measurement device according to a first preferred embodiment of the present invention.

Hereinafter, preferred embodiments of the present invention will be described in detail with reference to the drawings. Note that in the following preferred embodiments, identical or corresponding elements are given the same reference numerals in the drawings, and individual descriptions thereof will not be repeated.

Before describing the various preferred embodiments of the present invention, definitions will first be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. Meanwhile, "body axis" refers to an axis located along the direction in which the trunk area extends, or in other words, an axis extending in a direction approximately perpendicular to a side cross-section of the measurement subject's trunk area. "Trunk area width" corresponds to a dimension that is orthogonal to the body axis and that spans from the left to right ends of a horizontal cross-section of the trunk area, whereas "trunk area depth" corresponds to a dimension that is orthogonal to the body axis and that spans from the front to back ends of a horizontal cross-section of the trunk area. "Trunk area dimension", meanwhile, refers to either or both of the stated "trunk area width" and "trunk area depth". Note that it is preferable for the stated cross-section employed when determining the aforementioned "trunk area width" and "trunk area depth" to be a horizontal cross-section at an area of the trunk area that corresponds to the position of the navel.

First Preferred Embodiment

Figure 1B:
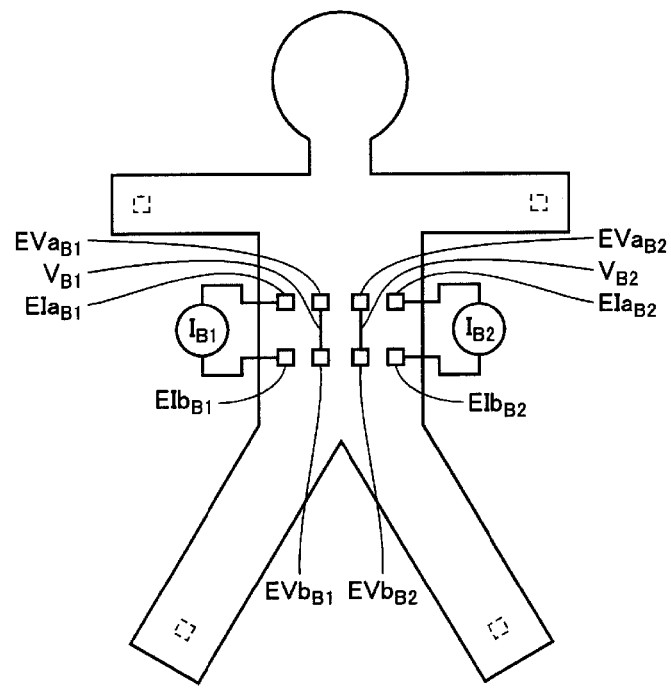
FIG. 1B is schematic a diagram illustrating the fundamentals of measurement performed by a body fat measurement device according to the first preferred embodiment of the present invention.

FIGS. 1A and 1B are schematic diagrams illustrating the fundamentals of measurement performed by a body fat measurement device according to a first preferred embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present preferred embodiment will be described with reference to FIGS. 1A and 1B. Note that FIGS. 1A and 1B both illustrate the measurement subject from the back side thereof.

As shown in FIG. 1A, electrodes $\text{EIa}_{A1}$ and $\text{EIa}_{A2}$ are attached to the surface of the left arm of the measurement subject and the surface of the right arm of the measurement subject, respectively, in order to obtain the body impedance for the entire trunk area. Likewise, electrodes $\text{EIb}_{A1}$ and $\text{EIb}_{A2}$ are attached to the surface of the left leg of the measurement subject and the surface of the right leg of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A, a total of eight electrodes, or electrodes $\text{EVa}_{A1}$, $\text{EVb}_{A1}$, $\text{EVa}_{A2}$, $\text{EVb}_{A2}$, $\text{EVa}_{A3}$, $\text{EVb}_{A3}$, $\text{EVa}_{A4}$, and $\text{EVb}_{A4}$, are attached to the back area surface of the measurement subject.

In this state, a constant current IA that passes through the trunk area is applied to the measurement subject using the electrodes $\text{EIa}_{A1}$, $\text{EIa}_{A2}$, $\text{EIb}_{A1}$, and $\text{EIb}_{A2}$ attached to both arms and both legs, respectively. While the constant current IA is applied, a potential difference $V_{A1}$ is detected using the pair of electrodes $\text{EVa}_{A1}$ and $\text{EVb}_{A1}$ attached to the back area surface, a potential difference $V_{A2}$ is detected using the pair of electrodes $\text{EVa}_{A2}$ and $\text{EVb}_{A2}$ attached to the back area surface, a potential difference $V_{A3}$ is detected using the pair of electrodes $\text{EVa}_{A3}$ and $\text{EVb}_{A3}$ attached to the back area surface, and a potential difference $V_{A4}$ is detected using the pair of electrodes $\text{EVa}_{A4}$ and $\text{EVb}_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current IA is flowing between both arms and both legs, which are positioned at a distance from the trunk area, and thus almost all of the applied constant current IA passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current IA is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in FIG. 1B, a total of eight electrodes, or electrodes $\text{EIa}_{B1}$, $\text{EIb}_{B1}$, $\text{EVa}_{B1}$, $\text{EVb}_{B1}$, $\text{EVa}_{B2}$, $\text{EVb}_{B2}$, $\text{EIa}_{B2}$, and $\text{EIb}_{B2}$, are attached to the back area surface of the measurement subject.

In this state, a constant current $I_{B1}$ that passes through the back area locally is applied to the measurement subject using the pair of electrodes $\text{EIa}_{B1}$ and $\text{EIb}_{B1}$, and a constant current $I_{B2}$ that passes through the back area locally is applied to the measurement subject using the pair of electrodes $\text{EIa}_{B2}$ and $\text{EIb}_{B2}$. While the constant currents $I_{B1}$ and $I_{B2}$ are applied, a potential difference $V_{B1}$ is detected using the pair of electrodes $\text{EVa}_{B1}$ and $\text{EVb}_{B1}$ attached to the back area surface, and a potential difference $V_{B2}$ is detected using the pair of electrodes $\text{EVa}_{B2}$ and $\text{EVb}_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential area differences $V_{B1}$ and $V_{B2}$ calculated in this manner. Note that if the body impedance Zs is found at this time by calculating the average value of the two stated potential differences $V_{B2}$ and $V_{B2}$, it is possible to reduce the influence of variations in the fat distribution within the surface layer area in the back area of the trunk area. Note that potential differences can also be measured in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B2}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \qquad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as 2xa and the depth of the trunk area is taken as 2xb, and because the trunk area has a generally oval cross-sectional shape, the trunk area cross-sectional area St can be approximated through the following Formula (2).

$$St = \pi \times a \times b \qquad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient α for reducing error. This coefficient α is obtained, for example, by finding the optimum value for α that fulfills St'=α×π×a×b, from the relationship between the stated a and b and a trunk area cross-sectional area St' obtained from a sample of a large number of X-ray CT images.

Accordingly, the stated Formula (2) can approximate with a lower degree of error through the following Formula (3) by using the coefficient α.

$$St = \alpha \times \pi \times a \times b \qquad \text{Formula (3)}$$

Note that it is preferable to optimize the coefficient α multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient α in accordance with the measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa = \beta \times a \times (1/Zt) \qquad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, β represents a coefficient for converting the body impedance Zt of the entire trunk area into the non-fat cross-sectional area Sa, and an optimum value can be found, for example, based on a sample of a large number of X-ray CT images, in the same manner as when finding the coefficient α. In other words, the optimum value for β that fulfils Sa'=β×a×(1/Zt) can be found from the relationship between a non-fat cross-sectional area Sa' obtained from a sample of a large number of X-ray CT images, the body impedance Zt of the entire trunk area of the measurement subject imaged by the X-ray CT, and the stated a.

Note that it is preferable for the stated coefficient β to be optimized as appropriate in accordance with the measurement subject information, in the same manner as the coefficient α mentioned above. In other words, the non-fat cross-sectional area Sa can be approximated with a higher degree of accuracy by changing the value of the stated coefficient β in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb = \gamma \times a \times Zs \qquad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, γ represents a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient α or the coefficient β. In other words, the optimum value for γ that fulfils Sb'=γ×a×Zs can be found from the relationship between a subcutaneous fat cross-sectional area Sb' obtained from a sample of a large number of X-ray CT images, the body impedance Zs of the surface layer area on the back area side of the trunk area of the measurement subject imaged by the X-ray CT, and the stated a.

Note that it is preferable for the stated coefficient γ to be optimized as appropriate in accordance with the measurement subject information, in the same manner as the coefficient α and the coefficient β mentioned above. In other words, the subcutaneous fat cross-sectional area Sb can be approximated with a higher degree of accuracy by changing the value of the stated coefficient γ in accordance with the measurement subject information.

As described thus far, in the body fat measurement device according to the present preferred embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx = \alpha \times \pi \times a \times b - \beta \times a \times (1/Zt) - \gamma \times a \times Zs \qquad \text{Formula (6)}$$

Figure 2:
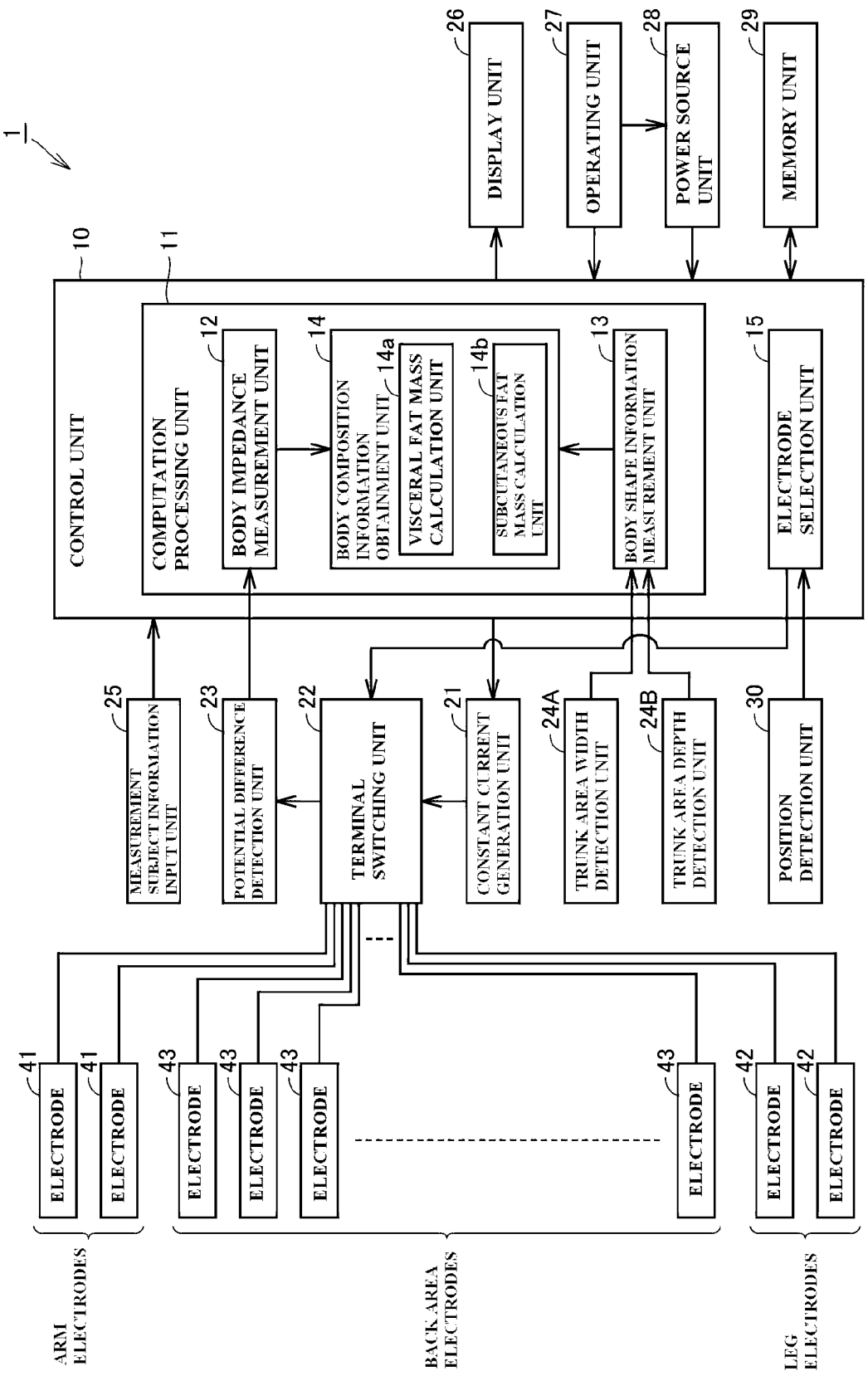
FIG. 2 is a block diagram illustrating the functional block configuration of the body fat measurement device according to the first preferred embodiment of the present invention.

FIG. 2 is a block diagram illustrating the functional block configuration of the body fat measurement device according to the present preferred embodiment. Next, the functional block configuration of the body fat measurement device according to the present preferred embodiment will be described with reference to FIG. 2.

As shown in FIG. 2, a body fat measurement device 1 according to the present preferred embodiment primarily includes: a control unit 10; a constant current generation unit 21; a terminal switching unit 22; a potential difference detection unit 23; a trunk area width detection unit 24A; a trunk area depth detection unit 24B; a measurement subject information input unit 25; a display unit 26; an operating unit 27;

a power source unit 28; a memory unit 29; a position detection unit 30; and multiple electrodes 41, 42, and 43 that are fitted to the body of the measurement subject. The control unit 10 includes a computation processing unit 11 and an electrode selection unit 15, and the computation processing unit 11 has a body impedance measurement unit 12, a body shape information measurement unit 13, and a body composition information obtainment unit 14.

The control unit 10 is configured of, for example, a CPU (Central Processor Unit), and is a unit for controlling the body fat measurement device 1 as a whole. Specifically, the control unit 10 outputs instructions to the various aforementioned functional blocks, accepts inputs of various types of information from the various aforementioned functional blocks, performs various types of computation processes based on the various types of information accepted, and so on. The various types of computation processes are carried out by the stated computation processing unit 11 provided in the control unit 10.

The aforementioned multiple electrodes include: arm electrodes 41 serving as upper limb electrodes placed in contact with surfaces of the upper limbs of the measurement subject; leg electrodes 42 serving as lower limb electrodes placed in contact with the surfaces of the lower limbs of the measurement subject; and back area electrodes 43 placed in contact with the back area surface of the measurement subject. Of these, the arm electrodes 41 are placed in contact with measurement subject's wrists, and the leg electrodes 42 are placed in contact with the measurement subject's ankles. Meanwhile, as shown in FIGS. 1A and 1B, the back area electrodes 43 are arranged in rows and placed in contact with the back area surface of the measurement subject. Note that the arm electrodes 41, leg electrodes 42, and back area electrodes 43 are all electrically connected to the terminal switching unit 22 described above.

The terminal switching unit 22 is configured of, for example, a relay circuit; based on instructions inputted from the electrode selection unit 15 of the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit operating based on instructions inputted from the electrode selection unit 15 of the control unit 10, electrodes from among the stated multiple electrodes 41, 42, and 43 function as the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A and the respective electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$ shown in FIG. 1B.

The constant current generation unit 21 generates a constant current based on an instruction inputted from the control unit 10, and supplies the generated constant current to the stated constant current application electrodes via the terminal switching unit 22. A high-frequency current (for example, 50 kHz, 500 µA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the body impedance measurement unit 12 of the control unit 10. Through this, the potential difference between the potential difference detection electrodes is detected in a state in which the aforementioned constant current is applied to the measurement subject.

The trunk area width detection unit 24A and trunk area depth detection unit 24B are detection units for measuring the trunk area width and trunk area depth, respectively, of the measurement subject without making contact therewith, and are configured of, for example, range sensors such as photoelectric sensors. The trunk area width detection unit 24A and the trunk area depth detection unit 24B output signals based on the values detected to the body shape information measurement unit 13. Note that in addition to photoelectric sensors, various types of non-contact range sensors that utilize ultrasound waves, electromagnetic waves, and the like (light, radio waves, magnetism, electrical fields, and so on of various wavelength bands, including laser light and visible light), movement amount detection sensors and the like that employ various types of encoders, and so on can be used as the stated range sensors.

The measurement subject information input unit 25 is a unit for obtaining information regarding the measurement subject used in computation processes carried out by the computation processing unit 11, and is configured of, for example, keys and the like that can be depressed by the measurement subject. Here, the measurement subject information includes at least one of the sex, age, height, weight, and so on of the measurement subject, as mentioned above. The measurement subject information input unit 25 accepts the input of measurement subject information, and outputs the accepted measurement subject information to the control unit 10. Note that the measurement subject information input unit 25 is not absolutely necessary in the configuration of the present invention, and whether or not to provide the measurement subject information input unit 25 can be determined based on whether or not it is necessary to use the measurement subject information in the computation processes performed by the computation processing unit 11.

The position detection unit 30 is a unit that detects a relative positional relationship between a trunk area dimension measurement unit 100A (mentioned later; see FIG. 3 and the like) and a back area electrode group support unit 200A (also mentioned later; see FIG. 3 and the like), and is configured of, for example, a movement amount detection sensor that employs various types of encoders or the like. The position detection unit 30 outputs a signal based on a detection value to the electrode selection unit 15. Note that in addition to the stated movement amount detection sensor that employs various types of encoders, various types of non-contact range sensors that utilize ultrasound waves, electromagnetic waves, and the like (light, radio waves, magnetism, electrical fields, and so on of various wavelength bands, including laser light and visible light), and so on can be used as the position detection unit 30.

The computation processing unit 11 includes the body impedance measurement unit 12, the body shape information measurement unit 13, and the body composition information obtainment unit 14, as mentioned above. The body composition information obtainment unit 14 functions as a body fat mass calculation unit, and includes a visceral fat mass calculation unit 14a and a subcutaneous fat mass calculation unit

14b. The body impedance measurement unit 12 calculates the body impedance based on a signal inputted from the potential difference detection unit 23, and outputs that body impedance to the body composition information obtainment unit 14. The body shape information measurement unit 13 calculates the width and the depth of the measurement subject's trunk area based on the signals inputted from the trunk area width detection unit 24A and the trunk area depth detection unit 24B, and outputs the calculated information to the body composition information obtainment unit 14. The body composition information obtainment unit 14 calculates and obtains the body composition information based on the body impedance inputted from the body impedance measurement unit 12, the width and depth of the trunk area inputted from the body shape information measurement unit 13, and in some cases, the measurement subject information inputted from the measurement subject information input unit 25 as well. More specifically, the visceral fat mass calculation unit 14a calculates a visceral fat mass and the subcutaneous fat mass calculation unit 14b calculates a subcutaneous fat mass.

The electrode selection unit 15 is a unit that selects specific electrodes from among the multiple electrodes 43 included in a back area electrode group; the electrode selection unit 15 selects the stated specific electrodes based on position information inputted from the stated position detection unit 30, and controls the operations of the terminal switching unit 22 so that the selected electrodes function as the stated constant current application electrodes or the potential difference detection electrodes.

The display unit 26 is configured of, for example, an LCD (Liquid Crystal Display) or the like, and displays the body composition information calculated by the body composition information obtainment unit 14 as mentioned above. More specifically, the visceral fat mass calculated by the visceral fat mass calculation unit 14a and the subcutaneous fat mass calculated by the subcutaneous fat mass calculation unit 14b are displayed in the display unit 26 based on signals outputted from the control unit 10. Here, in the body fat measurement device 1 according to the present preferred embodiment, the visceral fat mass is displayed as, for example, the visceral fat cross-sectional area, and the subcutaneous fat mass is displayed as, for example, the subcutaneous fat cross-sectional area.

The operating unit 27 is a unit through which the measurement subject inputs commands to the body fat measurement device 1, and is configured of, for example, buttons and the like that can be depressed by the measurement subject. Note that the operating unit 27 includes various types of operation buttons such as a power button, a measure button, and so on.

The power source unit 28 is a unit for supplying electrical power to the control unit 10, and uses an internal power source such as a battery, an external power source such as an AC outlet, or the like.

The memory unit 29 is configured of, for example, a random access memory (RAM) or a read-only memory (ROM), and is a unit for storing various types of data, programs, and the like for the body fat measurement device 1. The memory unit 29 stores, for example, the aforementioned measurement subject information, the calculated body composition information, a body composition information measurement program for executing a body composition information measurement process (mentioned later), and so on.

Figure 3:
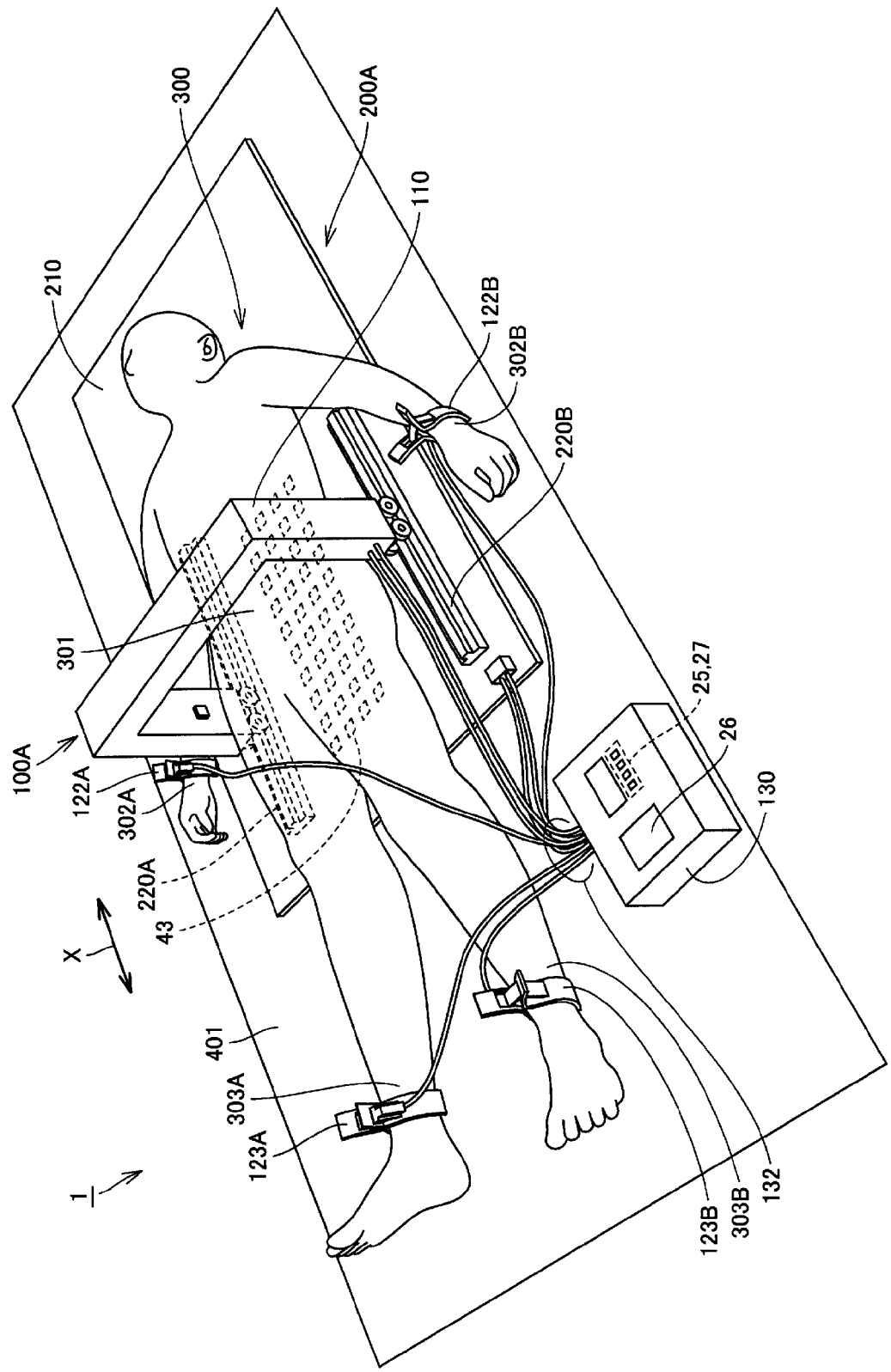
FIG. 3 is a perspective view illustrating the configuration of a body fat measurement device and a measurement position according to a first preferred embodiment of the present invention.
Figure 4:
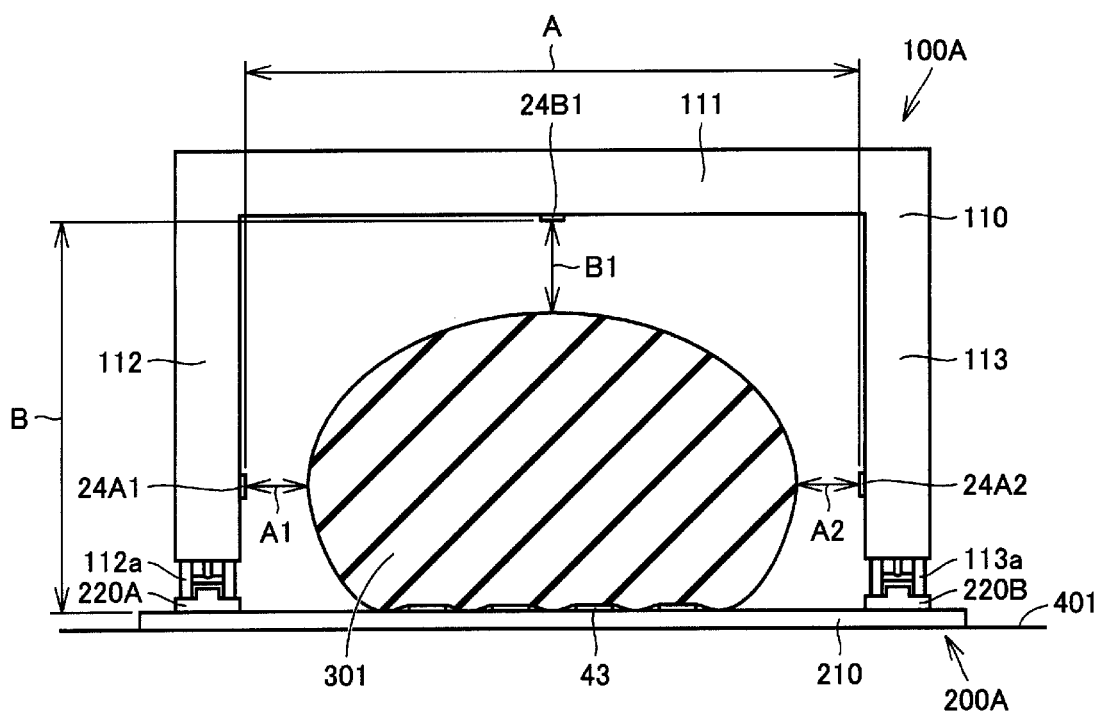
FIG. 4 is a schematic diagram illustrating the configuration of a trunk area dimension measurement unit in the body fat measurement device according to the first preferred embodiment of the present invention, and a method for measuring a trunk area width and a trunk area depth using the stated unit.

FIG. 3 is a perspective view illustrating the configuration of the body fat measurement device and a measurement position according to the present preferred embodiment. FIG. 4 is a schematic diagram illustrating the configuration of a trunk area dimension measurement unit in the body fat measurement device according to the present preferred embodiment, and a method for measuring a trunk area width and a trunk area depth using the stated unit. Next, the configuration of the body fat measurement device according to the present preferred embodiment, the measurement position, the configuration of the trunk area dimension measurement unit, a method for measuring the trunk area width and the trunk area depth using the stated device/unit, and so on will be described with reference to FIGS. 3 and 4.

First, the configuration of the body fat measurement device and the configuration of the trunk area dimension measurement unit according to the present preferred embodiment will be described with reference to FIGS. 3 and 4.

As shown in FIG. 3, the body fat measurement device 1 according to the present preferred embodiment primarily includes the trunk area dimension measurement unit 100A, the back area electrode group support unit 200A, a right arm fitting unit 122A, a left arm fitting unit 122B, a right leg fitting unit 123A, a left leg fitting unit 123B, and a main body unit 130. The aforementioned various functional blocks are provided in these units 100A, 200A, 122A, 122B, 123A, 123B, and 130. The main body unit 130 is electrically connected to each of the remaining other units 100A, 200A, 122A, 122B, 123A, and 123B by connection cables 132, and exchanges signals with the aforementioned various functional blocks via the connection cables 132.

The main body unit 130 is configured of a box-shaped unit on the top surface of which the measurement subject information input unit 25, the operating unit 27, the display unit 26, and so on are provided, and includes the stated control unit 10, constant current generation unit 21, terminal switching unit 22, potential difference detection unit 23, power source unit 28, memory unit 29, and so on.

The back area electrode group support unit 200A is configured of a sheet-shaped unit capable of being placed upon a bed surface 401 in an unrolled state, and includes an insulative mat 210, the multiple back area electrodes 43 disposed upon a primary surface of the mat 210, and a pair of guide rails 220A and 220B that serve as a guidance mechanism provided upon the primary surface of the mat 210. The back area electrodes 43 are provided so as to be arranged in matrix form on the mat 210, and the region in which the back area electrodes 43 are provided is configured so as to extend along the body axis direction of a measurement subject 300 who is lying face-up on the mat 210. Meanwhile, the guide rails 220A and 220B are provided so as to sandwich the region in which the back area electrodes 43 are provided in a direction orthogonal to the stated body axis direction of the measurement subject 300, and the respective guide rails 220A and 220B extend along the stated body axis direction of the measurement subject 300.

Here, although the number of back area electrodes 43 provided in the mat 210 is not particularly limited, it is assumed that the number provided is at least more that the number of back area electrodes 43 required for a single body fat measurement. In other words, for example, in the case where a total of eight (two rows by four columns) back area electrodes 43 are required for a single body fat measurement as shown in FIG. 1, a total of 12 (three rows by four columns) or more is taken as the minimum number of back area electrodes 43 provided on the mat 210.

The back area electrodes 43 are provided protruding slightly from the primary surface of the mat 210, so as to make contact with the back area surface on a trunk area 301 of the measurement subject 300 with certainty when the measurement subject 300 is in a position lying face-up on the mat 210. Note that the back area electrodes 43 provided in the back area electrode group support unit 200A are all connected to the terminal switching unit 22 provided in the main body unit 130 via the connection cables 132.

The right arm fitting unit 122A and the left arm fitting unit 122B are each configured of clip-shaped units, and are fitted onto a right arm 302A and a left arm 302B, respectively, of the measurement subject 300 during measurement. The arm electrodes 41 are provided in the right arm fitting unit 122A and the left arm fitting unit 122B, respectively. The arm electrodes 41 are provided in the right arm fitting unit 122A and the left arm fitting unit 122B, respectively, in an exposed manner, so as to make contact with the surfaces of the right arm and the left arm of the measurement subject 300 when the right arm fitting unit 122A and the left arm fitting unit 122B are fitted to the right arm 302A and the left arm 302B, respectively. Note that the arm electrodes 41 provided in the right arm fitting unit 122A and the left arm fitting unit 122B are all connected to the terminal switching unit 22 provided in the main body unit 130 via the connection cables 132.

The right leg fitting unit 123A and the left leg fitting unit 123B are each configured of clip-shaped units, and are fitted onto a right leg 303A and a left leg 303B, respectively, of the measurement subject 300 during measurement. The leg electrodes 42 are provided in the right leg fitting unit 123A and the left leg fitting unit 123B, respectively. The leg electrodes 42 are provided in the right leg fitting unit 123A and the left leg fitting unit 123B, respectively, in an exposed manner, so as to make contact with the surfaces of the right leg and the left leg of the measurement subject 300 when the right leg fitting unit 123A and the left leg fitting unit 123B are fitted to the right leg 303A and the left leg 303B, respectively. Note that the leg electrodes 42 provided in the right leg fitting unit 123A and the left leg fitting unit 123B are all connected to the terminal switching unit 22 provided in the main body unit 130 via the connection cables 132.

As shown in FIGS. 3 and 4, the trunk area dimension measurement unit 100A is configured of a gate-type unit having a frame shape that is capable of surrounding the trunk area 301 of the measurement subject 300 who is in a position lying face-up on the bed surface 401. More specifically, the trunk area dimension measurement unit 100A is configured of a frame member 110 that includes a bar-shaped upper frame portion 111, a bar-shaped right side frame portion 112, and a bar-shaped left side frame portion 113; casters 112a and 113a that serve as guidance mechanisms are provided on the bottom ends of the right side frame portion 112 and the left side frame portion 113, respectively. The casters 112a and 113a are capable of engaging with the aforementioned guide rails 220A and 220B provided in the back area electrode group support unit 200A, and as a result, the trunk area dimension measurement unit 100A is configured to be capable of moving along the body axis direction of the measurement subject 300 (an X direction indicated by the arrow in FIG. 3) upon the back area electrode group support unit 200A.

As shown in FIG. 4, range sensors 24A1 and 24A2, serving as the aforementioned trunk area width detection unit 24A, are attached to the respective inner surfaces of the right side frame portion 112 and the left side frame portion 113 in the trunk area dimension measurement unit 100A (that is, the surface of the trunk area dimension measurement unit 100A that faces the trunk area 301 of the measurement subject 300 when the trunk area dimension measurement unit 100A is disposed around the trunk area 301 of the measurement subject 300). Both of the range sensors 24A1 and 24A2 emit light toward the inner side of the trunk area dimension measurement unit 100A along the horizontal direction, and measure distances from the range sensors 24A1 and 24A2 to the trunk area 301 of the measurement subject 300, which is the area to be detected, by receiving light reflected therefrom. Note that the range sensors 24A1 and 24A2 provided in the trunk area dimension measurement unit 100A are all connected to the control unit 10 provided in the main body unit 130 via the connection cables 132.

Meanwhile, a range sensor 24B1, serving as the aforementioned trunk area depth detection unit 24B, is attached to the inner surface of the upper frame portion 111 in the trunk area dimension measurement unit 100A (that is, the surface of the trunk area dimension measurement unit 100A that faces the trunk area 301 of the measurement subject 300 when the trunk area dimension measurement unit 100A is disposed around the trunk area 301 of the measurement subject 300). The range sensor 24B1 emits light toward the inner side of the trunk area dimension measurement unit 100A along the vertical direction, and measure a distance from the range sensor 24B1 to the trunk area 301 of the measurement subject 300, which is the area to be detected, by receiving light reflected therefrom. Note that the range sensor 24B1 provided in the trunk area dimension measurement unit 100A is connected to the control unit 10 provided in the main body unit 130 via the connection cables 132.

Next, a measurement position to be assumed by the measurement subject when measuring a body fat mass such as a visceral fat mass using the body fat measurement device according to the present preferred embodiment will be described with reference to FIG. 3.

As shown in FIG. 3, during measurement, the measurement subject 300 lies face-up on the back area electrode group support unit 200A that has been unrolled and placed upon the bed surface 401. At this time, the location in which the measurement subject 300 lies is adjusted so that the back area surface makes contact with the back area electrodes 43 provided in the back area electrode group support unit 200A. However, at this time, it is not necessary to adjust the location in which the measurement subject 300 lies perfectly; that is, a location where the back area generally matches the area where the back area electrodes 43 are provided is sufficient. Then, the measurement subject 300 fits the right arm fitting unit 122A and the left arm fitting unit 122B to the wrist of the right arm 302A and the wrist of the left arm 302B, respectively, and fits the right leg fitting unit 123A and the left leg fitting unit 123B to the ankle of the right leg 303A and the ankle of the left leg 303B, respectively.

In this state, the position of the trunk area dimension measurement unit 100A is adjusted along the body axis direction so that a portion that contains the location of the navel is positioned around the trunk area 301. Through this, the trunk area width and the trunk area depth are measured using the trunk area dimension measurement unit 100A. Note that the movement of the trunk area dimension measurement unit 100A during the positioning utilizes the guide rails 220A and 220B and the casters 112a and 113a that engage therewith as the aforementioned guidance mechanism, and the movement operation may be performed by an assistant or by the measurement subject him/herself.

After this, the body impedance is measured using the electrodes 41, 42, and 43 provided in the back area electrode group support unit 200A, the right arm fitting unit 122A, the left arm fitting unit 122B, the right leg fitting unit 123A, and the left leg fitting unit 123B. As a result, an actual measurement of body fat, such as the visceral fat mass, is taken.

Next, a method for measuring the trunk area width and the trunk area depth using the trunk area dimension measurement unit provided in the body fat measurement device according to the present preferred embodiment will be described with reference to FIG. 4.

As shown in FIG. 4, the pair of range sensors 24A1 and 24A2 serving as the trunk area width detection unit 24A is used in the calculation of the trunk area width 2xa. In other words, the trunk area width 2xa of the measurement subject 300 is calculated through the following Formula (7) using a distance A1 (that is, a distance between the range sensor 24A1 provided in the right side frame portion 112 and the right side surface of the trunk area 301 of the measurement subject 300) and a distance A2 (that is, a distance between the range sensor 24A2 provided in the left side frame portion 113 and the left side surface of the trunk area 301 of the measurement subject 300) as detected by the pair of range sensors 24A1 and 24A2, and a predetermined distance A (that is, a distance between the range sensor 24A1 provided in the right side frame portion 112 and the range sensor 24A2 provided in the left side frame portion 113).

$$2xa = A - A1 - A2 \quad \text{Formula (7)}$$

Meanwhile, as shown in FIG. 4, the range sensor 24B1 serving as the trunk area depth detection unit 24B is used in the calculation of the trunk area depth 2xb. In other words, the trunk area depth 2xb of the measurement subject 300 is calculated based on the following Formula (8) using a distance B1 (that is, a distance between the range sensor 24B1 provided in the upper frame portion 111 and the front surface of the trunk area 301 of the measurement subject 300) as detected by the range sensor 24B1, and a predetermined distance B (that is, a distance between the range sensor 24B1 provided in the upper frame portion 111 and the mat 210).

$$2xb = B - B1 \quad \text{Formula (8)}$$

Figure 5:
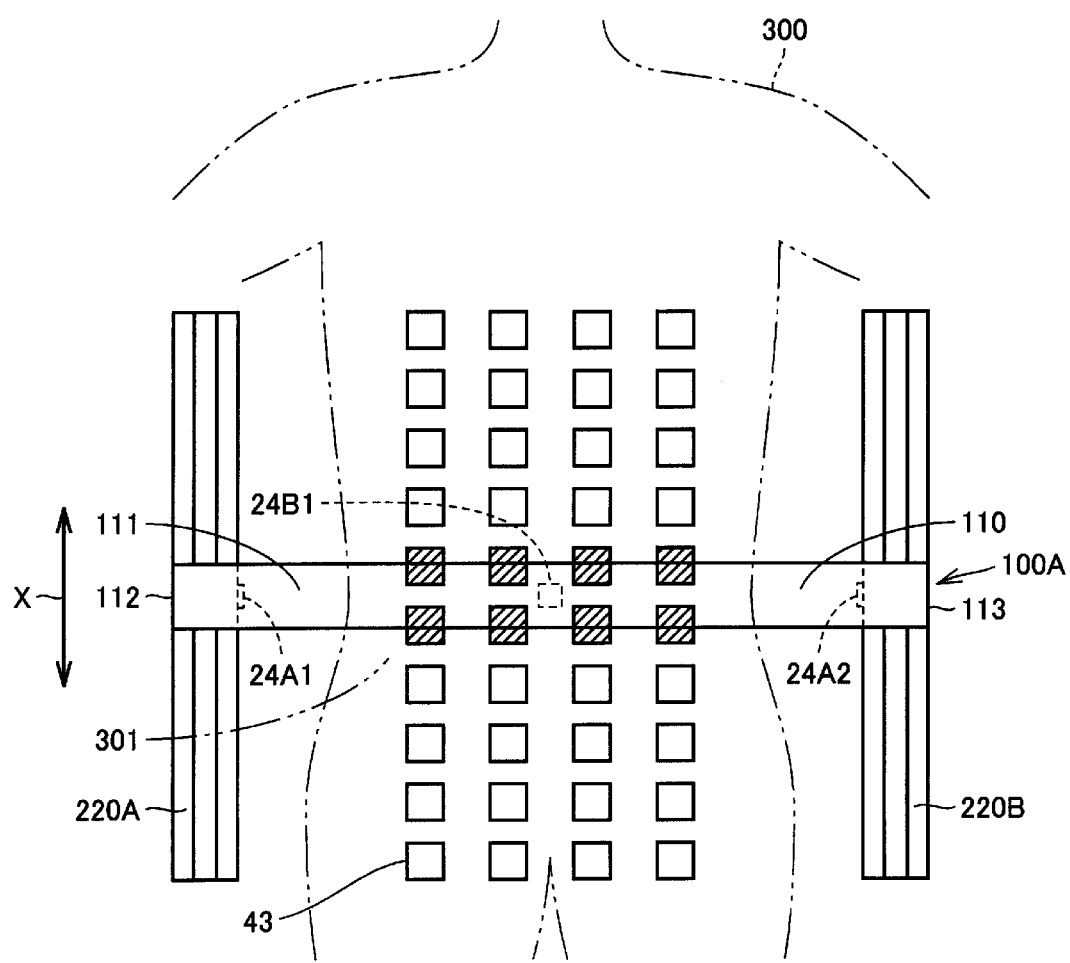
FIG. 5 is a schematic plan view illustrating an example of a state occurring after the trunk area dimension measurement unit in the body fat measurement device according to the first preferred embodiment of the present invention has been positioned.
Figure 6:
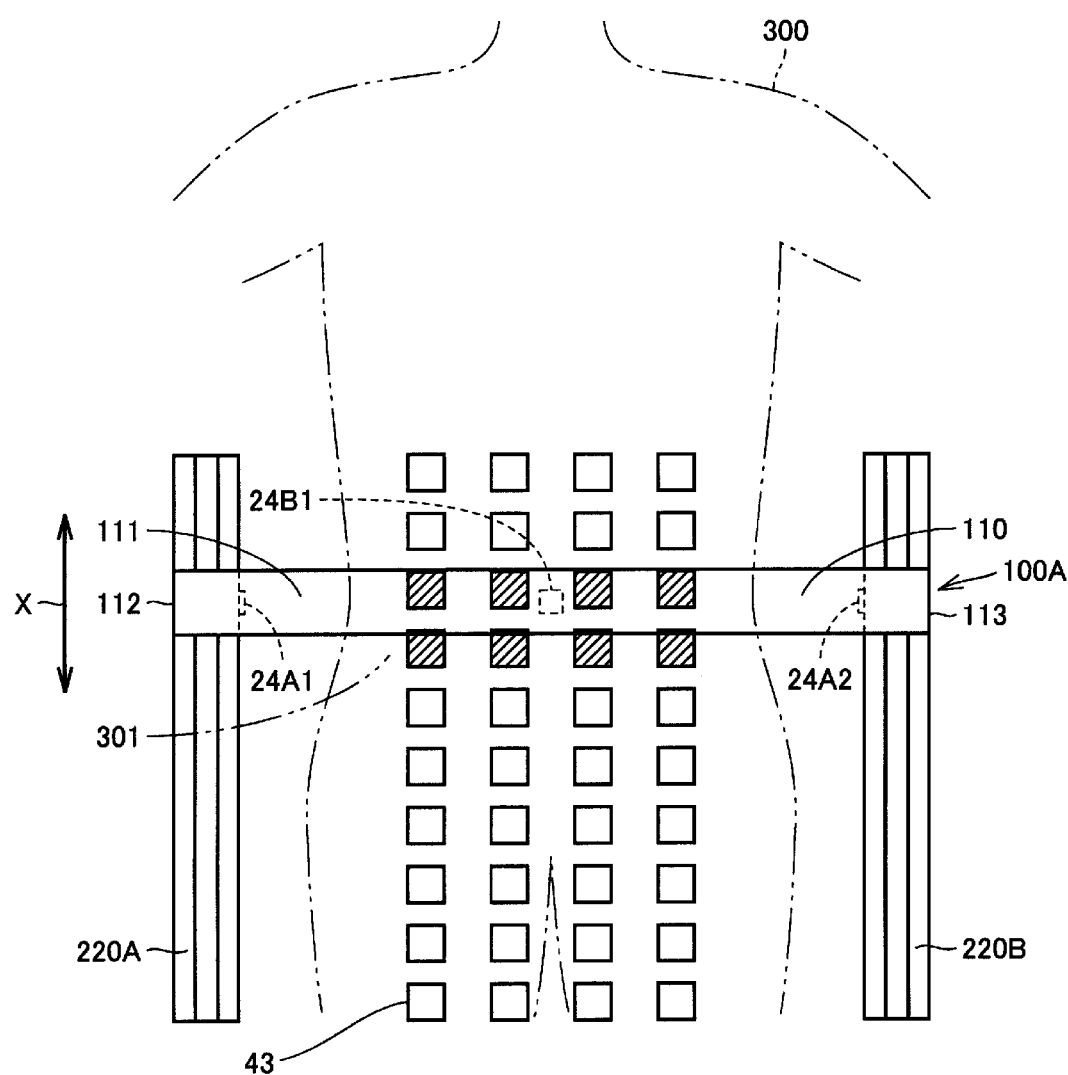
FIG. 6 is a schematic plan view illustrating another example of a state occurring after the trunk area dimension measurement unit in the body fat measurement device according to the first preferred embodiment of the present invention has been positioned.

FIGS. 5 and 6 are schematic plan views illustrating one example and another example of a state occurring after the trunk area dimension measurement unit in the body fat measurement device according to the present preferred embodiment has been positioned. Next, a method for selecting back area electrodes in the body fat measurement device according to the present preferred embodiment will be described in detail with reference to FIGS. 5 and 6.

As shown in FIG. 3, when the measurement subject 300 is in a measurement position lying face-up on the back area electrode group support unit 200A, the trunk area 301 of the measurement subject 300 is positioned in a region in which the back area electrode group is provided. As described above, in this state, the location in which the measurement subject lies is not perfectly adjusted along the body axis direction, and thus, for example, as shown in FIGS. 5 and 6, the positional relationship between the back area electrode group and the back area of the measurement subject 300 along the body axis direction will differ with each body fat measurement.

Here, as mentioned above, the body fat measurement device 1 according to the present preferred embodiment is configured so that the trunk area dimension measurement unit 100A is capable of moving along the body axis direction of the measurement subject 300 who is face-up on the back area electrode group support unit 200A, and during body fat measurement, the position is in the body axis direction is adjusted so that the trunk area dimension measurement unit 100A is disposed in a location corresponding to the location of the navel. Accordingly, after the position has been adjusted, the locating in which the trunk area dimension measurement unit 100A is present is a location that corresponds to the location of the navel of the measurement subject 300.

Accordingly, in the body fat measurement device 1 according to the present preferred embodiment, the position of the trunk area dimension measurement unit 100A relative to the back area electrode group support unit 200A is detected using the stated position detection unit 30, and based on the detected position information, the back area electrodes that are in contact with the part of the back area that corresponds to the location of the navel of the measurement subject 300 (that is, the back area electrodes indicated by hatching in FIGS. 5 and 6) are selected from the back area electrodes 43 that are provided in excess; the body impedance measurement is then carried out using the selected back area electrodes.

To be more specific, the electrode selection unit 15 refers to information of the position of the trunk area dimension measurement unit 100A relative to the back area electrode group support unit 200A inputted from the position detection unit 30 and drives the terminal switching unit 22 based on that information; as a result, the back area electrodes corresponding to the position in which the trunk area dimension measurement unit 100A is present are selectively connected to the constant current generation unit 21 or the potential difference detection unit 23, whereas the remaining unselected back area electrodes are not connected to the constant current generation unit 21 and the potential difference detection unit 23. Through this, of the multiple back area electrodes 43 included in the back area electrode group, only the back area electrodes in contact with the area corresponding to the location of the navel of the measurement subject 300 function as the constant current application electrodes or the potential difference detection electrodes, making it possible to measure the body impedance with a high degree of accuracy.

Note that a variety of conditions can be considered as specific conditions for selecting the back area electrodes, and for example, only the back area electrodes located below the trunk area dimension measurement unit 100A may be selected; alternatively, in the case where the back area electrodes are not positioned directly below the trunk area dimension measurement unit 100A, only the back area electrodes in the vicinity of locations on either side of the trunk area dimension measurement unit 100A in the body axis direction may be selected. Furthermore, in cases such as where the back area electrodes are disposed at a higher density, only the back area electrodes in locations on either side of the trunk area dimension measurement unit 100A in the body axis direction may be selected, without selecting the back area electrodes located directly below the trunk area dimension measurement unit 100A. In this manner, the conditions for selecting specific back area electrodes are not particularly limited, and any conditions may be used as long as the electrodes disposed in an area corresponding to the measurement subject's trunk area location where a trunk area dimension is detected using the trunk area dimension measurement unit 100A (that is, electrodes near the location of the measurement subject's navel in an area where the trunk area dimension is detected using the trunk area dimension measurement unit 100A).

As described thus far, and as shown in, for example, FIGS. 5 and 6, regardless of the positional relationship between the back area electrode group and the back area of the measurement subject 300 in the body axis direction, as long as the trunk area 301 in the area corresponding to the location of the navel of the measurement subject 300 is above the back area electrode group, the back area electrodes placed in contact with the back area in the area corresponding to the location of the navel can be used to measure the body impedance with a high degree of accuracy.

Figure 7:
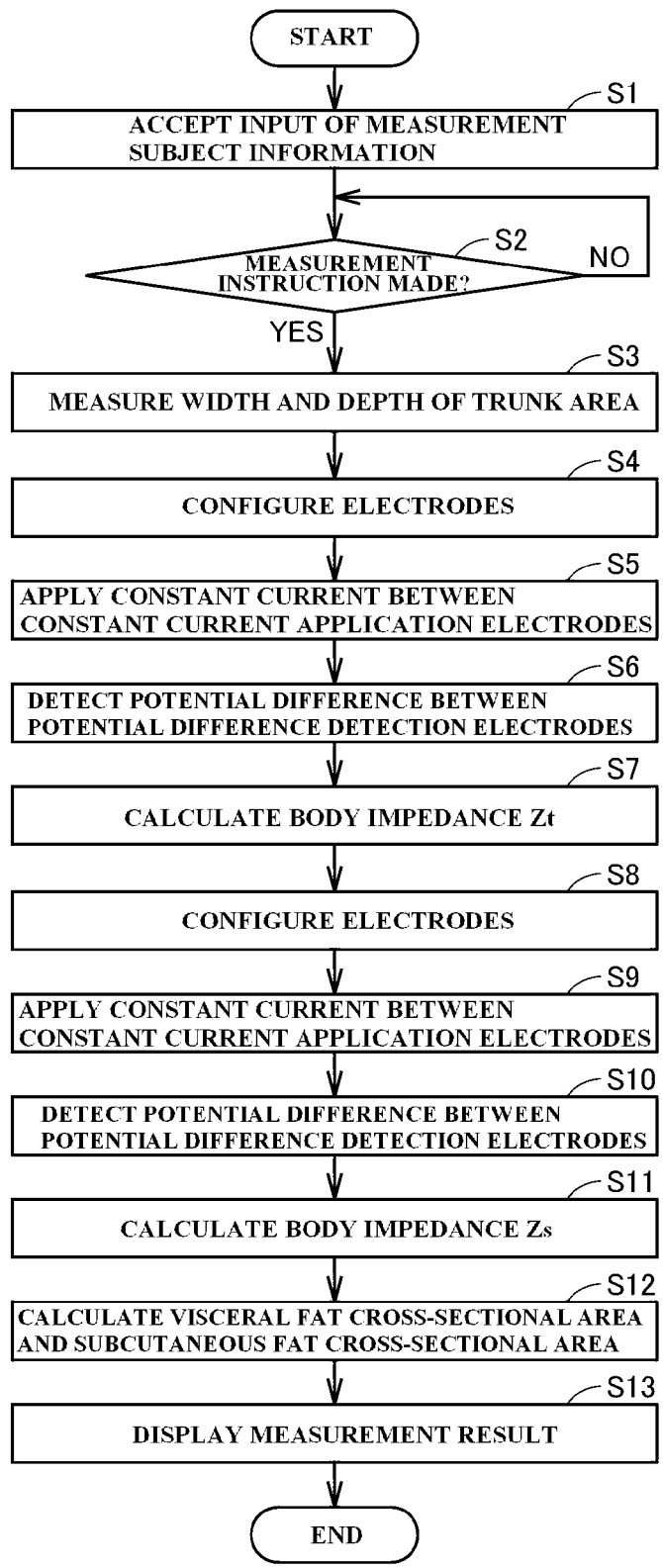
FIG. 7 is a flowchart illustrating a process performed by a control unit in the body fat measurement device according to the first preferred embodiment of the present invention.

FIG. 7 is a flowchart illustrating a process performed by the control unit in the body fat measurement device according to the present preferred embodiment. Next, a sequence of processes executed by the control unit of the body fat measurement device according to the present preferred embodiment will be described with reference to FIG. 7. Note that the processes indicated in the flowchart in FIG. 7 are stored in the memory unit 29 in advance as a program, and a visceral fat cross-sectional area measurement process and a subcutaneous fat cross-sectional area measurement process are realized by the control unit 10 when the control unit 10 including the computation processing unit 11 reads out and executes that program.

As shown in FIG. 7, the control unit 10 first accepts an input of the measurement subject information (step S1). The accepted measurement subject information is temporarily saved in, for example, the memory unit 29.

Next, the control unit 10 determines whether or not there has been an instruction to start the measurement (step S2). The control unit 10 stands by until there has been an instruction to start the measurement (NO in step S2), and advances to the next process in the case where an instruction to start the measurement has been detected (YES in step S2).

Next, the control unit 10 measures the width and depth of the trunk area (step S3). Specifically, the control unit 10 obtains the width 2xa and the depth 2xb of the trunk area of the measurement subject using the body shape information measurement unit 13, based on signals inputted from the trunk area width detection unit 24A and the trunk area depth detection unit 24B. The obtained width 2xa and depth 2xb of the trunk area of the measurement subject are temporarily saved in the memory unit 29.

Next, the control unit 10 configures the electrodes (step S4). Specifically, the control unit 10 selects specific back area electrodes from among the back area electrode group through the electrode selection unit 15 based on the position information inputted from the position detection unit 30, and outputs, based on the selection, an instruction to the terminal switching unit 22 to switch the electrodes; based on the instruction, the terminal switching unit 22 configures the multiple electrodes 41, 42, and 43 as the respective electrodes shown in FIG. 1A.

Next, the control unit 10 applies a constant current between the constant current application electrodes (step S5). Specifically, the control unit 10 outputs an instruction to the constant current generation unit 21 for generating the constant current, and based on this, the constant current generation unit 21 applies the constant current IA generated between the constant current application electrodes as shown in FIG. 1A.

Next, the control unit 10 detects a potential difference between the potential difference detection electrodes (step S6). Specifically, the control unit 10 outputs an instruction to the potential difference detection unit 23 for detecting a potential difference, and based on this, the potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 12.

Next, the control unit 10 calculates the body impedance Zt (step S7). Specifically, the control unit 10 calculates the body impedance Zt using the body impedance measurement unit 12, based on a signal inputted from the potential difference detection unit 23. The calculated body impedance Zt is temporarily saved in the memory unit 29.

Next, the control unit 10 reconfigures the electrodes (step S8). Specifically, the control unit 10 selects specific back area electrodes from among the back area electrode group through the electrode selection unit 15 based on the position information inputted from the position detection unit 30, and outputs, based on the selection, an instruction to the terminal switching unit 22 to switch the electrodes; based on the instruction, the terminal switching unit 22 configures the multiple electrodes 41, 42, and 43 as the respective electrodes shown in FIG. 1B.

Next, the control unit 10 applies a constant current between the constant current application electrodes (step S9). Specifically, the control unit 10 outputs an instruction to the constant current generation unit 21 for generating the constant current, and based on this, the constant current generation unit 21 applies the constant currents $I_{B1}$ and $I_{B2}$ generated between the constant current application electrodes as shown in FIG. 1B.

Next, the control unit 10 detects a potential difference between the potential difference detection electrodes (step S10). Specifically, the control unit 10 outputs an instruction to the potential difference detection unit 23 for detecting a potential difference, and based on this, the potential difference detection unit 23 detects the potential differences $V_{B1}$ and $V_{B2}$ between the potential difference detection electrodes shown in FIG. 1B, and outputs the detected potential differences to the body impedance measurement unit 12.

Next, the control unit 10 calculates the body impedance Zs (step S11). Specifically, the control unit 10 calculates the body impedance Zs using the body impedance measurement unit 12, based on a signal inputted from the potential difference detection unit 23. The calculated body impedance Zs is temporarily saved in the memory unit 29.

Next, the control unit 10 calculates the visceral fat cross-sectional area and the subcutaneous fat cross-sectional area (step S12). Specifically, the control unit 10 calculates the visceral fat cross-sectional area Sx as the visceral fat mass using the visceral fat mass calculation unit 14a and calculates the subcutaneous fat cross-sectional area Sb as the subcutaneous fat mass using the subcutaneous fat mass calculation unit 14b, based on the width 2xa and depth 2xb of the trunk area detected in step S3, the body impedance Zt calculated in step S7, and the body impedance Zs calculated in step S11. Note that the calculated visceral fat cross-sectional area Sx and subcutaneous fat cross-sectional area Sb are temporarily saved in the memory unit 29.

Then, the control unit 10 displays the measurement results (step S13). Specifically, the control unit 10 outputs, to the display unit 26, an instruction to display the visceral fat cross-sectional area Sx and subcutaneous fat cross-sectional area Sb calculated in step S12, and based on this, the display unit 26 displays those measurement results.

Through this, the body fat measurement device 1 completes the visceral fat cross-sectional area measurement process and the subcutaneous fat cross-sectional area measurement process.

As described in the foregoing, by employing the body fat measurement device 1 according to the present preferred embodiment, the body fat measurement can be carried out having automatically selected the optimal back area electrodes by positioning the trunk area dimension measurement unit 100A, even if the back area electrodes are not perfectly positioned and brought into contact with the back area of the measurement subject 300. Accordingly, by employing the aforementioned configuration, it is possible to realize a body fat measurement device that is capable of accurately measuring body fat masses such as visceral fat mass and that is easy to operate and use when taking such measurements. Moreover, by employing the aforementioned configuration, it is possible for the measurement subject to take measurements by him/herself without help from an assistant or the like, which makes it possible to realize a body fat measurement device that is suited to taking daily measurements of visceral fat masses or the like.

Second Preferred Embodiment

Figure 8:
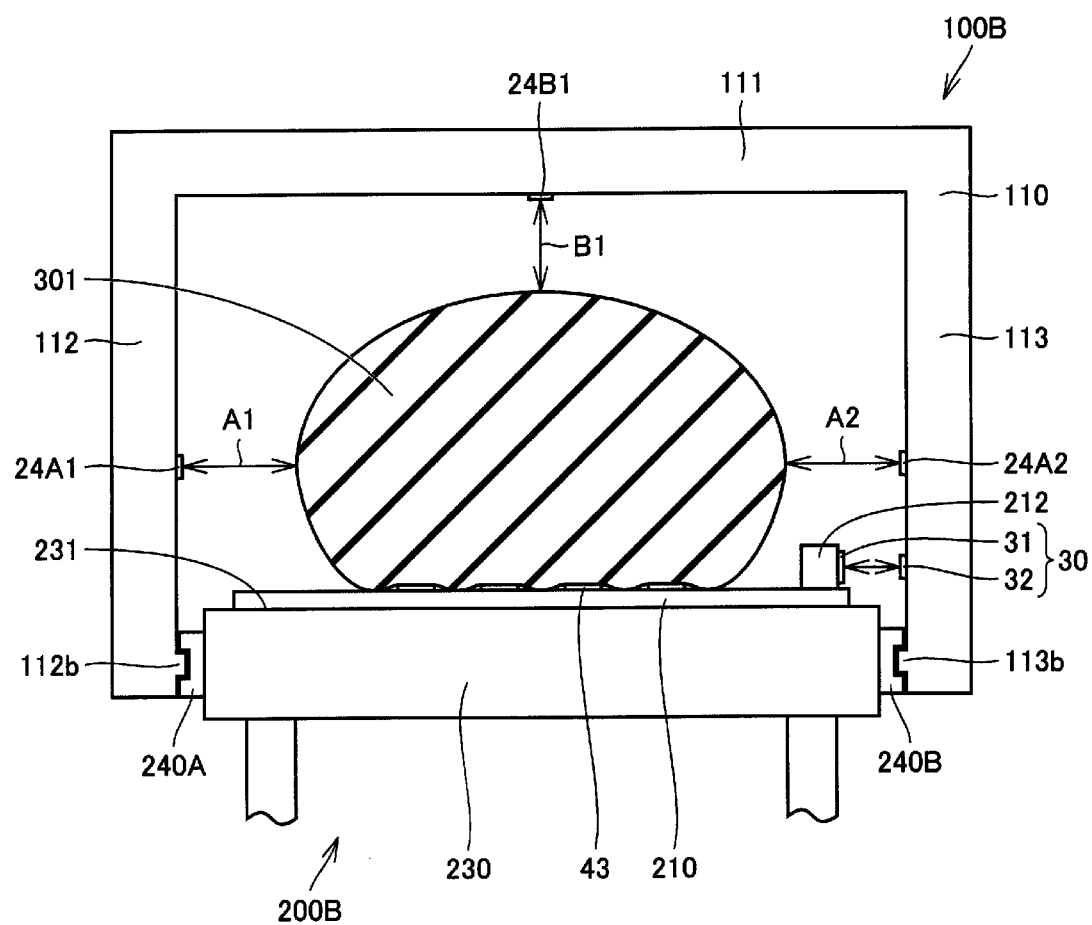
FIG. 8 is a schematic diagram illustrating the configuration of a trunk area dimension measurement unit in a body fat measurement device according to a second preferred embodiment of the present invention.

FIG. 8 is a schematic diagram illustrating the configuration of a trunk area dimension measurement unit and a back area electrode group support unit in a body fat measurement device according to a second preferred embodiment of the present invention. The body fat measurement device according to the present preferred embodiment has the same basic configuration as the body fat measurement device according to the aforementioned first preferred embodiment of the present invention, and differs only in terms of the specific configurations of the trunk area dimension measurement unit and back area electrode group support unit.

As shown in FIG. 8, a trunk area dimension measurement unit 100B of the body fat measurement device according to the present preferred embodiment is the same as the trunk area dimension measurement unit 100A according to the aforementioned first preferred embodiment in terms of the configuration of the gate-type unit having a frame shape that includes the upper frame portion 111, the right side frame portion 112, and the left side frame portion 113; however, the configuration differs from that of the trunk area dimension measurement unit 100A in that casters are not provided on the bottom ends of the right side frame portion 112 and the left side frame portion 113. Instead of the casters, engagement portions 112b and 113b that protrude inward and serve as a guidance mechanism are provided in predetermined locations of the bottom ends of the right side frame portion 112 and the left side frame portion 113 of the trunk area dimension measurement unit 100B.

Meanwhile, a back area electrode group support unit 200B in the body fat measurement device according to the present preferred embodiment includes a bed 230 in addition to the mat 210 and the multiple back area electrodes 43 provided therein, and the mat 210 is unrolled and placed upon a bed surface 231 of the bed 230. The back area electrode group support unit 200B in the body fat measurement device according to the present preferred embodiment differs from the back area electrode group support unit 200A in the aforementioned first preferred embodiment in that guide rails are not provided on the mat 210; instead, guide rails 240A and 240B that serve as a guidance mechanism for engaging with the engagement portions 112b and 113b provided in the trunk area dimension measurement unit 100B are provided on the side surfaces of the bed 230.

The guidance mechanism configured of the engagement portions 112b and 113b provided in the trunk area dimension measurement unit 100B and the guide rails 240A and 240B provided in the back area electrode group support unit 200B guides the trunk area dimension measurement unit 100A so as to be capable of movement along the body axis direction.

Here, in the body fat measurement device according to the present preferred embodiment, a projecting portion 212 is provided on the mat 210 of the back area electrode group support unit 200B, and an indicator 31 (for example, an encoder strip such as a barcode or the like) indicating a position is affixed to the projecting portion 212. Meanwhile, a reading sensor 32 (for example, a photointerrupter or the like) capable of reading the stated indicator is disposed is an area of the trunk area dimension measurement unit 100B that opposes the projecting portion 212.

The indicator 31 and the reading sensor 32 correspond to the position detection unit 30 (see FIG. 2) that detects the relative positional relationship between the trunk area dimension measurement unit 100B and the back area electrode group support unit 200B, and the back area electrodes are selected by the electrode selection unit 15 based on position information detected by the position detection unit 30.

Even when such a configuration is employed, the same effects as the effects of the aforementioned body fat measurement device according to the first preferred embodiment of the present invention can be achieved. In other words, with the body fat measurement device according to the present preferred embodiment, it is possible to realize a body fat measurement device that is capable of accurately measuring body fat masses such as visceral fat mass and that is easy to operate and use when taking such measurements.

Although the first and second preferred embodiments of the present invention described thus far provide examples of body fat measurement devices configured to be capable of taking actual measurements of both the trunk area width and the trunk area depth, in the case where another measurement means is provided and an actual measurement of the circumferential length of the trunk area (waist length) can be taken, the case where the device is configured so that the circumferential length of the trunk area is inputted as the measurement subject information, and so on, the device may be configured so that an actual measurement is taken of only one of the trunk area width and the trunk area depth, the other of the trunk area width and the trunk area depth is calculated based on the circumferential length of the trunk area, and a body fat mass is calculated based thereon.

In addition, although the aforementioned first and second preferred embodiments of the present invention describe examples in which the computation processing unit is configured so as to calculate the visceral fat cross-sectional area as the visceral fat mass and the subcutaneous fat cross-sectional area as the subcutaneous fat mass, the computation processing unit may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

In addition, although the aforementioned first and second preferred embodiments of the present invention describe examples in which the configuration is such that both the visceral fat cross-sectional area and the subcutaneous fat cross-sectional area are calculated and displayed, the configuration may be such that only one of these indicators is displayed, or that only the subcutaneous fat cross-sectional area is calculated and displayed. Furthermore, the configuration may be such that various types of body composition information aside from the visceral fat cross-sectional area and the subcutaneous fat cross-sectional area (for example, the body fat mass, area-by-area fat mass, fat-free mass, and so on) are calculated and displayed.

In this manner, the preferred embodiments and variations disclosed herein are to be understood in all ways as exemplary and in no ways limiting. The technical scope of the present invention is defined by the appended claims, and all variations that fall within the meaning and range of equivalency of the claims are intended to be embraced therein.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A body fat measurement device comprising:
   a trunk area electrode group including a plurality of electrodes for making contact with a surface of a measurement subject's trunk area;
   a trunk area electrode group support unit, in which said trunk area electrode group is provided, for bringing at least some of the plurality of electrodes included in said trunk area electrode group into contact with the measurement subject's trunk area;
   a trunk area dimension detection unit for detecting a trunk area dimension of the measurement subject;
   a trunk area dimension measurement unit in which said trunk area dimension detection unit is provided;
   a position detection unit that detects a relative positional relationship between said trunk area electrode group support unit and said trunk area dimension measurement unit;
   an electrode selection unit that selects specific electrodes from the plurality of electrodes included in said trunk area electrode group based on the position information detected by said position detection unit;
   a body impedance measurement unit that measures a body impedance of the measurement subject's body using the electrodes selected by said electrode selection unit;
   a body fat mass calculation unit that calculates a body fat mass based on the body impedance measured by said body impedance measurement unit and the trunk area dimension detected by said trunk area dimension detection unit;
   wherein said trunk area electrode group support unit is configured as a mat that can be disposed below the measurement subject's trunk area when the measurement subject is lying down; and
   said trunk area dimension measurement unit is configured as a frame-shaped member that can be disposed so as to surround the measurement subject's trunk area when the measurement subject is lying down.

2. The body fat measurement device according to claim 1, further comprising:
   a guidance mechanism that guides said trunk area dimension measurement unit so as to be movable along a body axis direction of the measurement subject's trunk area.

3. The body fat measurement device according to claim 1, wherein the plurality of electrodes included in said trunk area electrode group are disposed in rows on a primary surface of said mat.

4. The body fat measurement device according to claim 1, wherein said trunk area dimension detection unit is a non-contact range sensor disposed on said frame-shaped member.

5. The body fat measurement device according to claim 1, wherein said trunk area dimension measurement unit is disposed so as to be positioned at the location of the measurement subject's navel during measurement.

6. The body fat measurement device according to claim 1, wherein said electrode selection unit selects, as said specific electrodes, electrodes, from among the plurality of electrodes included in said trunk area electrode group, that are disposed in an area corresponding to the location of the measurement subject's trunk area at which the trunk area dimension is detected using said trunk area dimension measurement unit.

7. The body fat measurement device according to claim 1, wherein the plurality of electrodes included in said trunk area electrode group are electrodes for making contact with a surface of a back area that is an area of the measurement subject's trunk area on a back side.

8. The body fat measurement device according to claim 1, wherein the body fat mass calculation unit includes at least one of a visceral fat mass calculation unit that calculates the visceral fat mass of the measurement subject and/or a subcutaneous fat mass calculation unit that calculates the subcutaneous fat mass of the measurement subject.

* * * * *